United States Patent
Fujii et al.

(10) Patent No.: US 9,340,680 B2
(45) Date of Patent: May 17, 2016

(54) SPINEL POWDER AND MANUFACTURING PROCESS THEREFOR, AND PROCESSES FOR PRODUCING THERMAL SPRAYING FILM AND GAS SENSOR ELEMENTS

(75) Inventors: Namitsugu Fujii, Yokkaichi (JP); Ryo Nishizawa, Yokkaichi (JP); Takuji Nabeta, Osaka (JP)

(73) Assignees: DAIICHI KIGENSO KAGAKU KOGYO CO., LTD., Osaka-shi (JP); DENSO CORPORATION, Kariya, Aichi-pref. (JP)

( * ) Notice: Subject to any disclaimer, the term of this patent is extended or adjusted under 35 U.S.C. 154(b) by 297 days.

(21) Appl. No.: 14/113,453

(22) PCT Filed: Mar. 29, 2012

(86) PCT No.: PCT/JP2012/058442
§ 371 (c)(1),
(2), (4) Date: Oct. 23, 2013

(87) PCT Pub. No.: WO2012/147449
PCT Pub. Date: Nov. 1, 2012

(65) Prior Publication Data
US 2014/0050842 A1    Feb. 20, 2014

(30) Foreign Application Priority Data

Apr. 28, 2011   (JP) .................................. 2011-102162

(51) Int. Cl.
C09D 1/00 (2006.01)
G01N 27/407 (2006.01)
C01F 7/16 (2006.01)

(52) U.S. Cl.
CPC . C09D 1/00 (2013.01); C01F 7/162 (2013.01); C23C 4/11 (2016.01); G01N 27/407 (2013.01); *C01P 2002/32* (2013.01); *C01P 2002/72* (2013.01); *C01P 2004/03* (2013.01); *C01P 2004/51* (2013.01); *C01P 2004/61* (2013.01); *C01P 2006/12* (2013.01); *Y10T 428/2991* (2015.01)

(58) Field of Classification Search
None
See application file for complete search history.

(56) References Cited

U.S. PATENT DOCUMENTS

| 3,544,266 A | * | 12/1970 | Dokuzoguz ............. | C01F 7/162 264/332 |
| 2008/0145306 A1 | | 6/2008 | Riedel et al. | |
| 2012/0175825 A1 | * | 7/2012 | Iwasaki ................ | C01G 23/003 264/603 |

FOREIGN PATENT DOCUMENTS

| JP | 56-109822 A | 8/1981 |
| JP | 2008-535750 A | 9/2008 |
| JP | 2008-286810 A | 11/2008 |
| JP | 2009-084093 A | 4/2009 |
| JP | 2010-138050 A | 6/2010 |
| WO | WO-2010/059070 A1 | 5/2010 |
| WO | 2011007852 * | 1/2011 |

OTHER PUBLICATIONS

L.B. Kong et al., "$MgAl_2O_4$ spinel phase derived from oxide mixture activated by a high-energy ball milling process", Materials Letters 56(3) 238-243.
Kipyung Ahn et al., "Spinel humidity sensors prepared by thermal spray direct writing", Sensors and Actuators B 107 (2005) 342-346.
Notice of Reasons for Rejection issued Sep. 30, 2014 in corresponding CN Application No. 2011-102162 (with English translation).
Masanobu Ezoe, Properties and Applications of Spinel for Refractories, TAIKABUTSU, 43 [1] 29-37 (1991) with translation thereof.
Idalia Gomez et al., Comparative study of microwave and conventional processing of $MgAl_2O_4$-based materials, Ceramics International, 2004, vol. 30, pp. 893-900.
G. Bertrand et al., "Dried particle plasma spray in-flight synthesis of spinel coating," Journal of the European Ceramic Society, 2002, vol. 22, pp. 891-902.
International Search Report for PCT/JP2012/058442, ISA/JP, mailed May 1, 2012.

* cited by examiner

*Primary Examiner* — Steven Bos
(74) *Attorney, Agent, or Firm* — Harness, Dickey & Pierce, P.L.C.

(57) ABSTRACT

Disclosed is a spinel powder obtained by mixing a magnesia raw-material with an electrically fused alumina, followed by firing of the mixture. The particles of the spinel powder are coated with granular spinel particles. Therefore, there are provided a spinel powder and a simple method for producing the same, which is superior in thermal spraying property and has a unique particle shape. In particular, there is provided a method for producing a spinel powder which contributes to a reduction in the variation of characteristics of sensors, for example, as a thermal spraying powder for forming a protective coating of a gas sensor element.

16 Claims, 13 Drawing Sheets

SPINEL POWDER AND MANUFACTURING PROCESS THEREFOR, AND PROCESSES FOR PRODUCING THERMAL SPRAYING FILM AND GAS SENSOR ELEMENTS

CROSS-REFERENCE TO RELATED APPLICATIONS

This application is a U. S. National Stage of International Application No. PCT/JP2012/058422, filed on Mar. 29, 2012 and published in Japanese as WO 2012/147449 on Nov. 1, 2012. This application is based on and claims priority to Japanese Patent Application No. 2011-102162, filed on Apr. 28, 2011. The entire disclosures of the above applications are incorporated by reference herein.

TECHNICAL FIELD

The present invention relates to a spinel powder and a method for producing the same, and methods for producing a thermal sprayed film and a gas sensor element.

BACKGROUND ART

Spinels which are comprised of magnesia and alumina (MgO—$Al_2O_3$ spinels) (simply referred to hereinafter as "spinels") have high degrees of heat resistance and crystal stability, and as one of their applications, have been used for long years as an electrode protecting film of a gas sensor element for detecting concentrations of oxygen in an internal-combustion engine. For example, there is known a gas sensor element as described in JP 2008-286810 A, in which a plasma-sprayed film using a spinel powder is used as an electrode protecting film of an oxygen sensor element. The oxygen sensor element consists of a cup-shaped solid electrolyte inside which a reference-gas area is provided, a measurement electrode which is provided on the outer surface of the solid electrolyte and is contacted with a gas to be measured, and a reference electrode which is provided on the inner surface of the solid electrolyte. In addition, a plasma-sprayed film using a spinel powder is placed, as a protective film, on the outside of the measurement electrode. In the oxygen sensor element, a heater which generates heat by electric current is also inserted into and positioned in the reference-gas area. The oxygen sensor element cannot detect concentrations of oxygen unless it reaches a temperature of or above a certain level. Heating by the heater enables the oxygen sensor element to measure the oxygen concentration in a gas even under conditions where the external atmosphere is at low temperatures. The mechanism by which the concentration of oxygen is detected is that an exhaust gas diffuses through the plasma-sprayed film to the electrode and reacts thereon, whereby an output is generated.

However, conventional oxygen sensor elements have problems as described below. That is, plasma spraying is a process by which a film is formed on the surface of an element by introducing a spinel powder into a plasma flame having a temperature of more than 5,000° C., and allowing the powder to be melted in a very short residence time, and thus the spinel powder does not stably melt, resulting in variation in the porosity of thermal sprayed films. Consequently, there is a problem that the responsiveness of sensors is varied. Factors responsible for the variation of the porosity include the stability of plasma flame, for example. Also, there is a problem concerning the particle shape of a spinel powder. The particles of a spinel powder have a flat surface and receive heat from a high-temperature plasma flame in a moment, and thus it is believe that the spinel powder particles have a poor efficiency of receiving heat, resulting in variation of their melting property. As a result, characteristics of gas sensors are varied.

The above-described feature that the surface of a spinel powder is flat results from the method for manufacturing the powder. For example, a spinel powder is produced as follows: a powder of an alumina raw-material and a powder of a magnesia raw-material are heated and melted temporarily in an electric furnace, and temporarily reacted and solidified to form a spinel, which is then subjected to pulverization and classification to a given particle diameter. In this case, the pulverizing of the spinel is performed by crushing it by mechanical impact. Thus, surfaces which have been broken by crushing stress are yielded, whereby the surface of the spinel powder becomes flat.

For stable use in a thermal spray process, use is made of a spinel powder of which the particle size has been adjusted to suit the thermal spray process. The adjustment of the particle size presents a problem of increasing the cost of a powder used in thermal spraying, because after a spinel which has been produced by an electric melting process is pulverized, only particles of the powder which fall within a given range of particle sizes by subjecting the powder to classification are used and particles falling beyond the range are discarded.

In order to meet a future exhaust-gas regulation, there also is a need for precise control of the composition of exhaust gas, for example. As for gas sensors, it is necessary to reduce the variation of their characteristics and the fluctuation of their durability characteristics. Gas sensor elements based on conventional structures have difficulties in meeting these requirements. In this connection, Masanobu Ezoe, TAIKABUTSU (Refractories), 43 [1], 29-37 (1991) describes the mechanism of spinel formation, which will be discussed below.

PRIOR ART DOCUMENTS

Patent Documents

Patent Document 1: JP 2008-286810 A

Non-Patent Documents

Non-Patent Document 1: Masanobu Ezoe, TAIKABUTSU (Refractories), 43 [1], 29-37 (1991)

DISCLOSURE OF THE INVENTION

Problems to be Solved by the Invention

In order to solve the problems described above, the present invention provides a spinel powder and a method for producing the same, which is superior in thermal spraying property, improves the performance of coatings, and can be produced at a reduced cost, as well as a method for producing a thermal sprayed film, and a method for producing a gas sensor element.

Means for Solving the Problems

The present inventors have made much investigation to solve the above-described problems. As a result, the present inventors have found that a spinel powder which is superior in thermal spraying property and has a unique particle shape can be obtained by mixing a magnesia raw-material to an electrically fused alumina, followed by firing of the mixture.

Furthermore, since electrically fused alumina finds a very wide range of applications such as abrasives and refractories, particles of a powder of electrically fused alumina which cannot be used in thermal spraying after the powder is subjected to classification for thermal spraying can be utilized in other applications, and thus the electrically fused alumina powder can be utilized very inexpensively. In addition, since a spinel is produced by mixing a magnesia raw-material using such a classified, electrically fused alumina and subjecting the mixture to firing, the total cost is reduced and a spinel powder exhibiting superior thermal spraying properties can be provided.

Based on these findings, the present invention provides the following inventions (1) to (10):

(1) A spinel powder coated with granular spinel particles.
(2) The spinel powder according to the above (1), wherein the granular spinel particles are from about 0.1 to 4 μm.
(3) The spinel powder according to the above (1) or (2), wherein the spinel powder has a mean particle diameter D50 of about 10 to 70 μm and a specific surface area of about 0.2 to 2 m$^2$/g.
(4) The spinel powder according to any one of the above (1) to (3), wherein the spinel powder has an alumina content of 69 to 82% and a magnesia content of 18 to 31%.
(5) The spinel powder according to any one of the above (1) to (4), wherein the spinel powder has X-ray diffraction intensity ratios:
a ratio $I[\alpha Al_2O_3(113)]/\{I[\alpha Al_2O_3(113)]+I[MgAl_2O_4(311)]\}$ of about 0.03 or less, and
a ratio $I[MgO(200)]/\{I[MgO(200)]+I[MgAl_2O_4(311)]\}$ of about 0.03 or less.
(6) A method for producing a spinel powder, which comprises mixing a magnesia raw-material with an electrically fused alumina, followed by firing of the mixture.
(7) The method for producing the spinel powder according to the above (6), wherein the spinel powder has an alumina content of 69 to 82% and a magnesia content of 18 to 31%.
(8) The method for producing the spinel powder according to the above (6) or (7), wherein the electrically fused alumina has a mean particle diameter D50 of about 7 to 70 μm and the magnesia raw-material has a mean particle diameter D50 of about 1 to 10 μm.
(9) A method for producing a thermal sprayed film, which comprises performing thermal spraying using a spinel powder, the spinel powder being produced by mixing a magnesia raw-material with an electrically fused alumina, followed by firing of the mixture.
(10) A method for producing a gas sensor element, which comprises forming an electrode-protecting film of the gas sensor element using a spinel powder, the spinel powder being produced by mixing a magnesia raw-material with an electrically fused alumina, followed by firing of the mixture.

Effects of the Invention

According to the present invention, it is possible to provide a spinel powder and a simple method for producing the same, which is superior in thermal spraying property and has a unique particle shape. In particular, there can be provided a method for producing a spinel powder which contributes to a reduction in the variation of characteristics of sensors, for example, as a thermal spraying powder for forming a protective coating of a gas sensor element. Such a spinel powder can be suitably used in these application fields.

MODE FOR CARRYING OUT THE INVENTION

The following gives a detailed explanation on a spinel powder and a method for producing the same according to the present invention. In the present invention, "%" refers to % by weight, unless otherwise indicated, and % by weight is equivalent to % by mass.

1. Spinel Powder

A spinel powder of the present invention is characterized in that a particle of the spinel powder is coated with granular spinel particles. The size (particle diameter) of the granular spinel particles is preferably about 0.1 to 4 μm, and particularly 0.3 to 3 μm, on average. In the present invention, however, the presence of a certain amount of spinel particles not falling within the above-described size range does not cause any particular problems.

Figure 1:
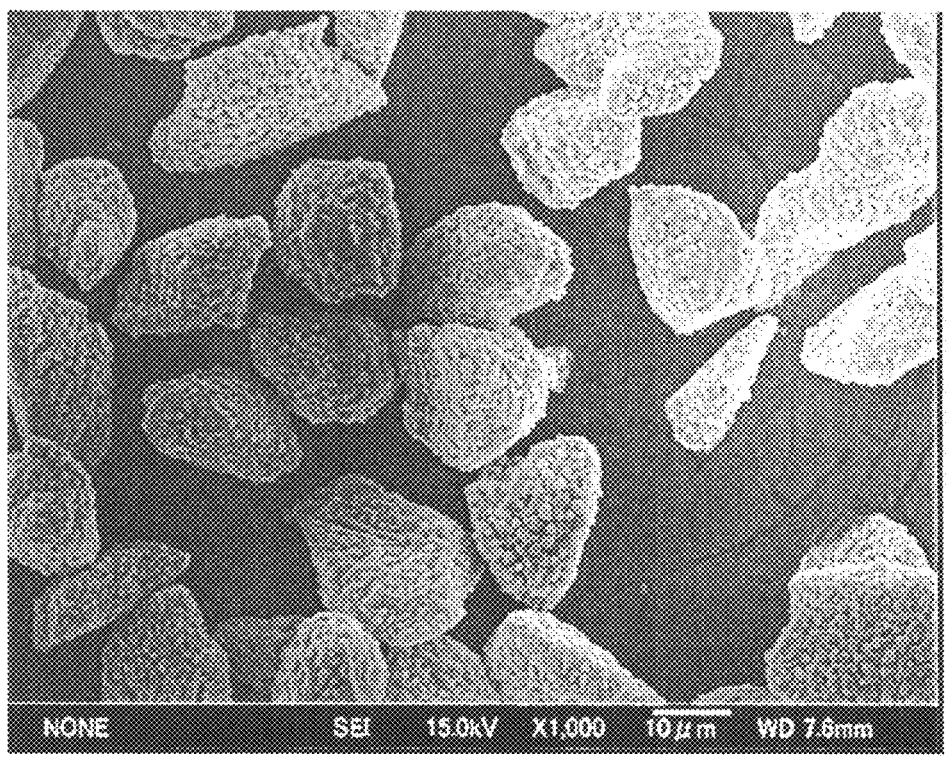
FIG. 1 is a micrograph (at a magnification of 1,000 times) of particles of the spinel powder obtained in Example 1.
Figure 2:
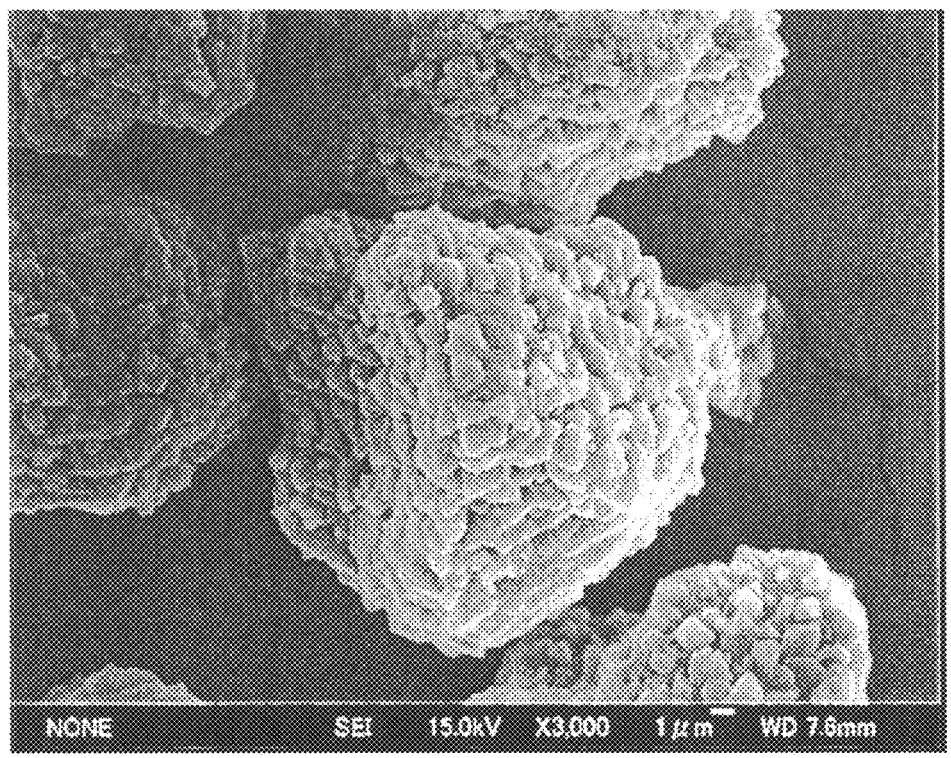
FIG. 2 is a micrograph (at a magnification of 3,000 times) of a particle of the spinel powder obtained in Example 1.
Figure 3:
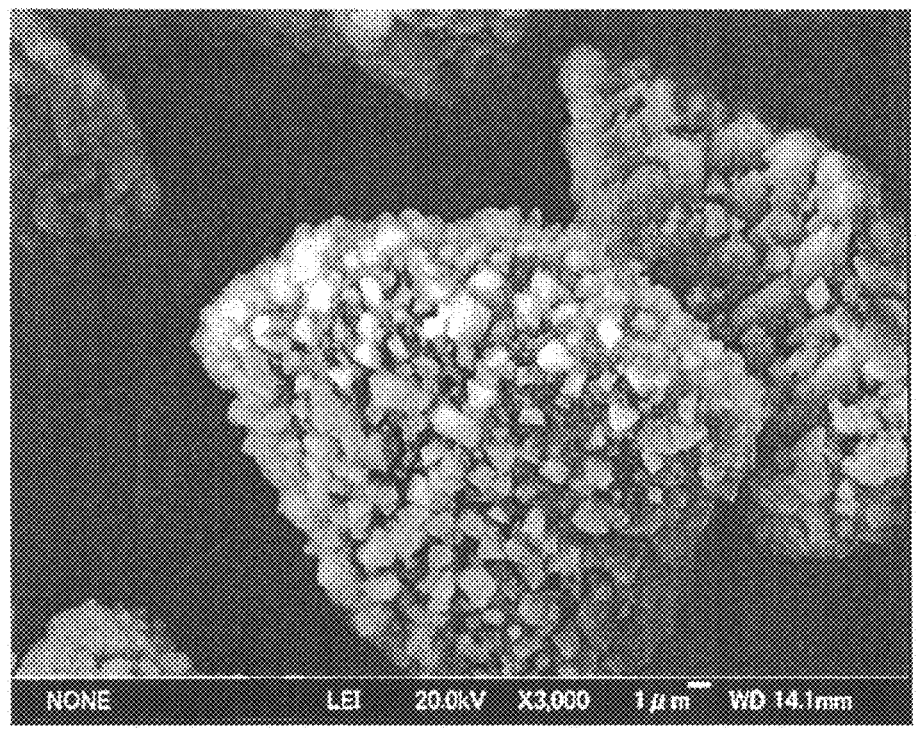
FIG. 3 is a micrograph (at a magnification of 3,000 times) of a particle of the spinel powder obtained in Example 1.
Figure 4:
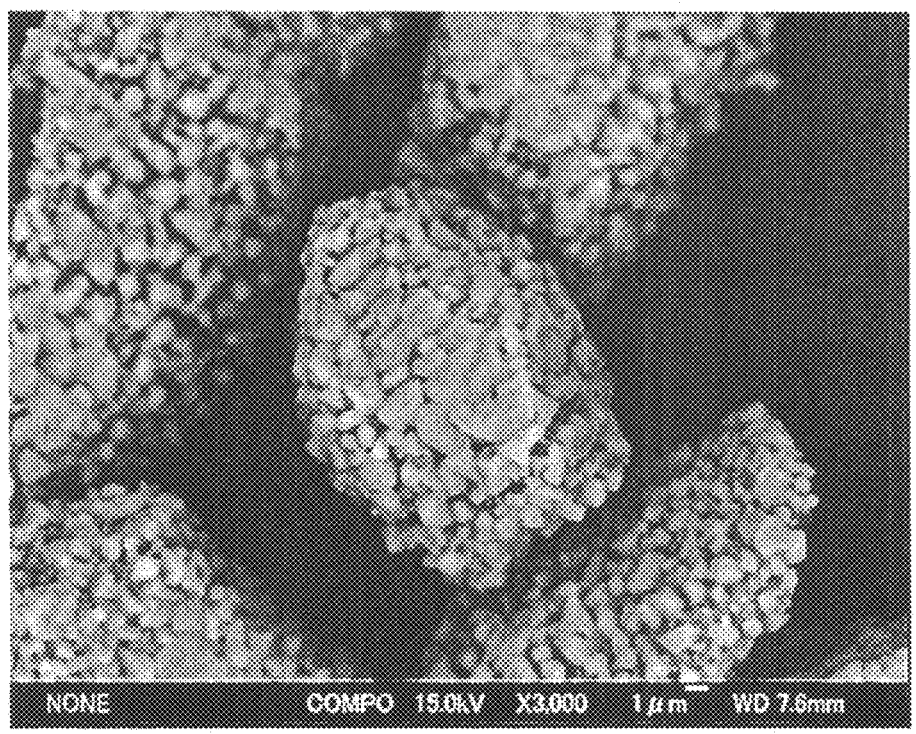
FIG. 4 is a micrograph (at a magnification of 3,000 times) of a particle of the spinel powder obtained in Example 2.

Typical particle shapes of a spinel powder of the present invention are shown in FIG. 1 (particles of the spinel powder obtained in Example 1, at a magnification of 1,000 times), in FIG. 2 (a particle of the spinel powder obtained in Example 1, at a magnification of 3,000 times), in FIG. 3 (a particle of the spinel powder obtained in Example 1, at a magnification of 3,000 times), and in FIG. 4 (a particle of the spinel powder obtained in Example 2, at a magnification of 3,000 times).

Figure 5:
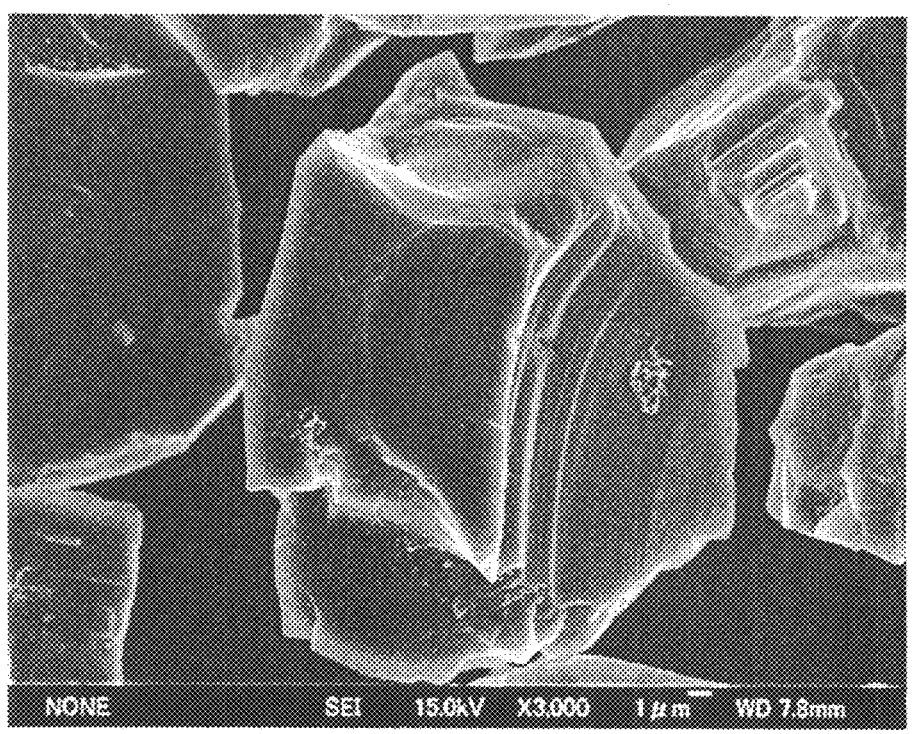
FIG. 5 is a micrograph (at a magnification of 3,000 times) of a particle of the spinel powder obtained by an electric melting process.
Figure 6:
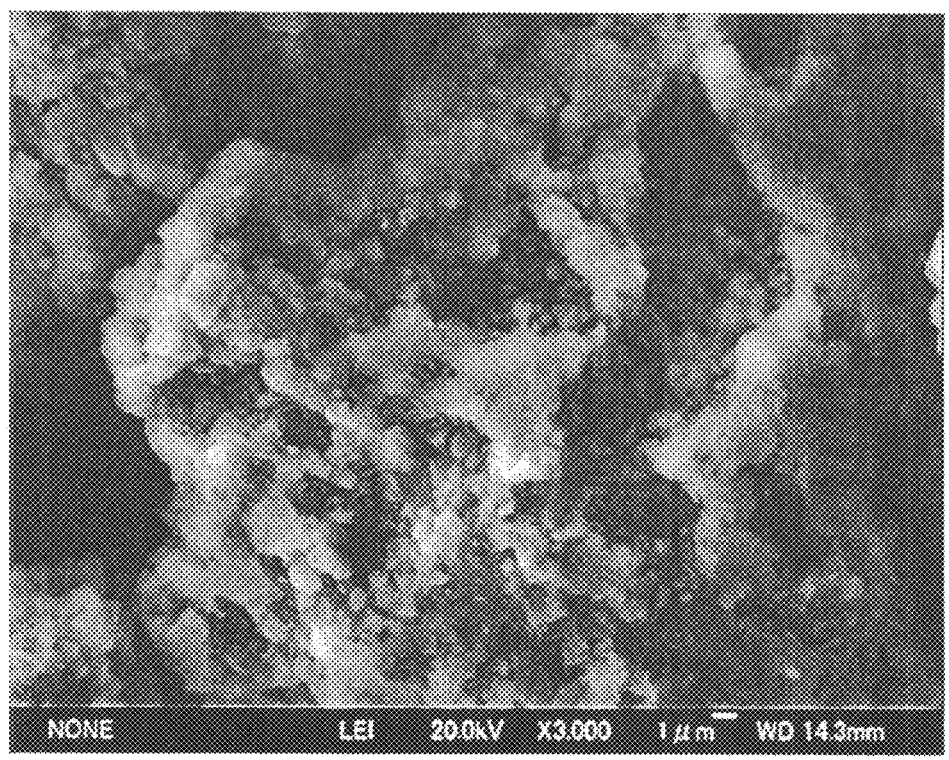
FIG. 6 is a micrograph (at a magnification of 3,000 times) of a particle of the spinel powder obtained by a sintering process.

As shown in FIG. 1, granular spinel particles are formed such that the surface of each particle of an electrically fused alumina used as a raw material is coated therewith, whereas each particle shown in FIG. 5 of a spinel powder, which was produced by an electric melting process, is dense inside and has a flat surface. Some types of spinel powder may be produced by sintering processes. The particle shown in FIG. 6 of a spinel powder, which was produced by a sintering process, seems to have a slightly uneven surface. The spinel powder produced by this process comprises particles within which cavities, holes, or the like are present (but the spinel powder of the present invention comprises particles which have no cavities, holes, or the like, and are dense inside), and such cavities and the like within the particles are not involved during thermal spraying, resulting in an increase in porosity, whereby a desired value of porosity may be not obtained. In the present invention, therefore, a sintered spinel can be used only when a porous film is required.

As is apparent from FIGS. 2 to 4, there are particles having a variety of shapes, although these particles are referred to as being "granular." In the present invention, these particles are collectively described as "granular", and even particles with some deformations are not problematic at all.

Further, it is apparent from FIGS. 2 to 4 that granular spinel particles that are about 0.1 to 4 μm are present on the surface of a particle of the spinel powder, which is coated therewith.

In the present invention, it is preferable that the content of alumina in the spinel powder is 69 to 82% and the content of magnesia in the spinel powder is 18 to 31%. If a spinel powder has a content of alumina and of magnesia in these respective ranges, then the spinel powder allows the formation of a suitable thermal sprayed coating which is superior in thermal spraying property.

The theoretical composition of spinel represented by $MgAl_2O_4$ is 71.7% of alumina and 28.3% of magnesia, but in the scope of the above-described (1), the spinel powder of the present invention has X-ray diffraction intensity ratios:
a ratio $I[\alpha Al_2O_3(113)]/\{I[\alpha Al_2O_3(113)]+I[MgAl_2O_4(311)]\}$ of about 0.03 or less, and
a ratio $I[MgO(200)]/\{I[MgO(200)]+I[MgAl_2O_4(311)]\}$ of about 0.03 or less.

In the specification, the above-described contents of alumina and magnesia are values from an experimental determination of the range where a spinel powder upon firing at 1,600° C. for 4 hours has X-ray diffraction intensity ratios:
a ratio $I[\alpha Al_2O_3(113)]/\{I[\alpha Al_2O_3(113)]+I[MgAl_2O_4(311)]\}$ of about 0.03 or less, and
a ratio $I[MgO(200)]/\{I[MgO(200)]+I[MgAl_2O_4(311)]\}$ of about 0.03 or less,
and is likely to have an error of the order of ±0.5%, including analytical errors and others.

It should be noted that since a spinel powder has X-ray diffraction intensity ratios which vary with its firing temperature (the intensity ratios would be in equilibrium after more than 2 hours of firing), the contents of alumina and magnesia in a spinel powder also vary with its firing temperature. For example, when the firing has been performed at 1,400° C. for 4 hours, the contents of alumina and magnesia will become narrower: the alumina content is 69.5 to 74.0% and the magnesia content is 26.0 to 30.5%; when firing has been performed at 1,250° C. for 4 hours, the alumina content is 71.0 to 73.5% and the magnesia content is 26.5 to 29.0%.

Unique shapes as described above of the particles of a spinel powder of the present invention are likely to be due to the method for producing it. The reason why a spinel powder of the present invention has a unique particle shape would be as explained below, by extrapolation based on micrographs taken in Example 1.

Figure 7:
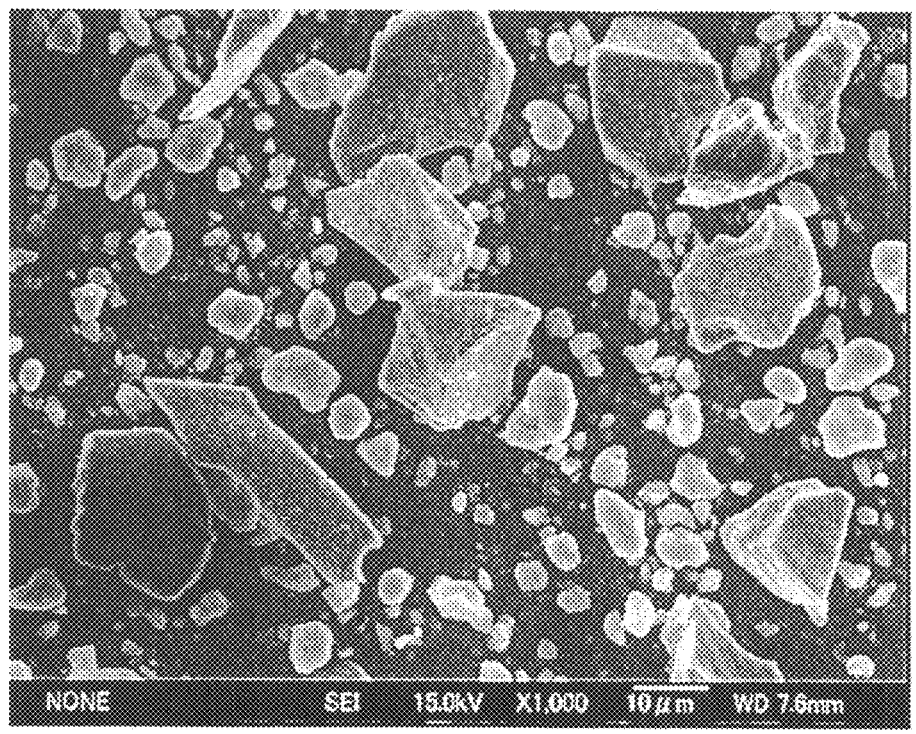
FIG. 7 is a micrograph (at a magnification of 1,000 times) of particles when an electrically fused alumina and a magnesium oxide were mixed in Example 1.

FIG. 7 is a micrograph (at a magnification of 1,000 times) of particles when a powder of an electrically fused alumina having a mean particle diameter of 20.6 μm and a powder of magnesium oxide having a mean particle diameter of 7 μm were only mixed. It is found from this micrograph that relatively larger particles of the electrically fused alumina are present and fine granular particles of the magnesium oxide are simply distributed around a particle of the alumina.

Based on this, it turns out that when mixed, the electrically fused alumina powder and the magnesium oxide powder did not cause any intra-particle changes and were simply mixed.

Thus, it is believed that within the mixture, the granular magnesium oxide particles are in point-to-point or face-to-face contact with a plurality of electrically fused alumina particles, in addition to between magnesium oxide particles, and a plurality of magnesium oxide particles are in point-to-point or face-to-face contact on the surface of a particle of the electrically fused alumina in a vertical, horizontal, or other manner.

Then, the mixture was subjected to firing. Calcination at 1,250° C. for 4 hours resulted in the formation of particles as shown in FIGS. 1, 2, and 3; and firing at 1,400° C. for 4 hours resulted in the formation of particles as shown in FIG. 4. From these, it is supposed that for electrically fused alumina particles and magnesium oxide particles which are in point-to-point or face-to-face contact with each other, as the firing proceeds, counterdiffusion of $Mg^{2+}$ and $Al^{3+}$ ions takes place at the contact between an electrically fused alumina particle and a magnesium oxide particle, at the same time as which the spinelization proceeds.

The document referred to above, Masanobu Ezoe, TAIKABUTSU (Refractories), 43 [1], 29-37 (1991), describes, on page 32 thereof, as follows: "Yamaguchi et al. reported that in the production of a spinel by reaction of MgO with $Al_2O_3$, oxygen ions do not easily diffuse and both $Mg^{2+}$ and $Al^{3+}$ ions counter-diffuse through fixed oxygen lattices, and that with regard to a spinel produced by contacting a monocrystalline $Al_2O_3$ powder with a monocrystalline MgO powder, followed by heat treatment in air at 1500° C., the $Al_2O_3$ portion of the contact portion allows a spinel to be produced by a topotaxial mechanism in which during its production the stacking of oxygen ions is changed from a hexagonal close-packed structure to a cubic close-packed structure thereby to have a specific directional relationship three-dimensional relative to the $Al_2O_3$ crystal, and the MgO portion of the contact portion allows a spinel to be produced by an epitaxial mechanism despite the fact that both the MgO and the spinel have an arrangement of oxygen ions with a cubic close-packed structure, and concluded that the ratio of the spinel produced in the MgO portion to that in the $Al_2O_3$ portion is 1:19/4 (FIG. 4)." According to this document, the reaction at the boundary between the spinel and the MgO is represented by the following equation:

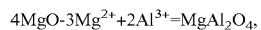

$$4MgO-3Mg^{2+}+2Al^{3+}=MgAl_2O_4,$$

and the spinel and the $Al_2O_3$ is represented by the following equation:

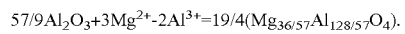

$$57/9Al_2O_3+3Mg^{2+}-2Al^{3+}=19/4(Mg_{36/57}Al_{128/57}O_4).$$

Figure 8:
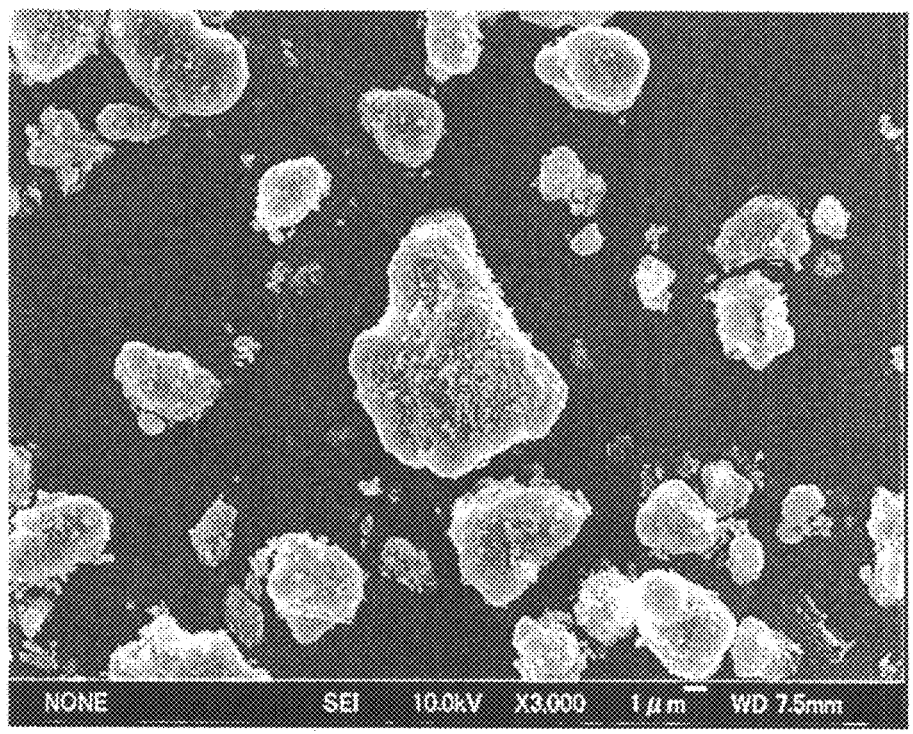
FIG. 8 is a micrograph (at a magnification of 3,000 times) of particles of the magnesia used in Example 1.
Figure 9:
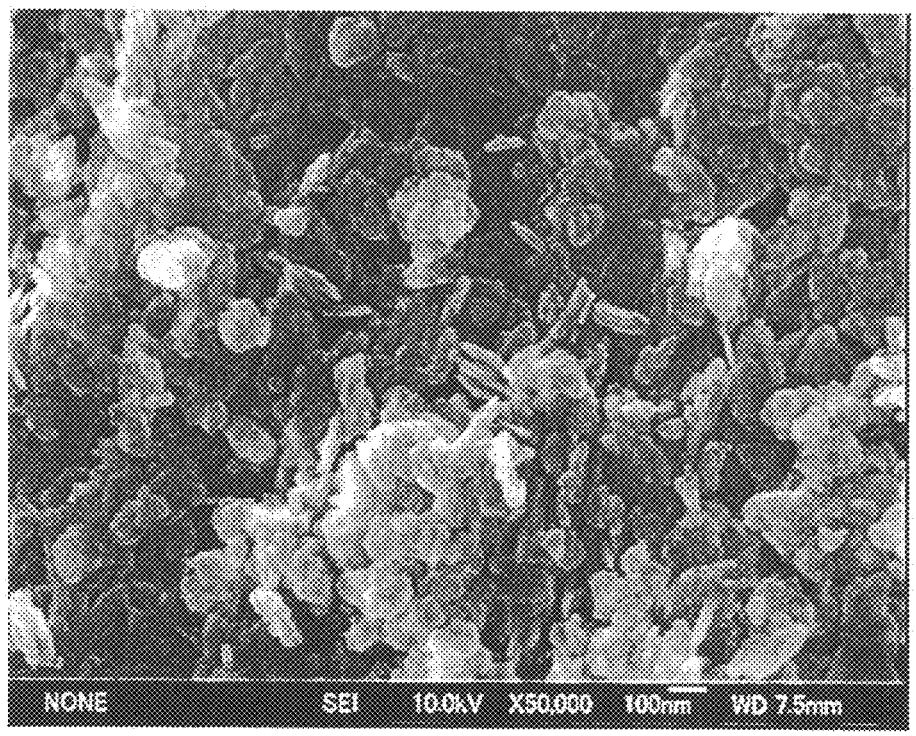
FIG. 9 is a micrograph (at a magnification of 50,000 times) of a particle of the magnesia used in Example 1.

FIGS. 8 and 9 show a micrograph of particles of the magnesia used in Example 1. FIG. 8 is a micrograph at a magnification of 3,000 times, and as far as can be judged from this micrograph, the particles seem like normal solid particles. When viewed at a magnification of 50,000 times in FIG. 9, the particle consists of secondary or tertiary agglomerated particles in which very small "granular" primary particles of about 0.03 to 0.2 μm have been agglomerated, and the presence of cavities can be observed. From these, the magnesia used in Example 1 could be considered to be a porous material inside which cavities are present. Therefore, even though the mean particle diameter D50 is 7 μm, the particle diameter would substantially be smaller.

Given that the surface of the magnesia used in Example 1 has an appearance of being granular with very small sizes, it is inferred that as described in the above-mentioned Ezoe's document, the alumina portion allows the generation of the topotaxial effect that the reaction occurs while the shape and crystal structure are essentially retained, and magnesia is epitaxially provided by diffusion from its surrounding with retaining granular shapes of the surface of the magnesia, and in consequence a spinel powder of particles, each of is coated with granular spinel particles as shown in FIG. 2 may be formed.

It is also inferred that a alumina particle which is in point-to-point contact with a magnesia particle having a large mean particle diameter D50 allows proceeding of their spinelization with counterdiffusion of $Mg^{2+}$ and $Al^{3+}$ ions, and at the same time, also proceeding of the condensation of the magnesia particle, which is porous, and thus there may be formed a spinel powder of particles, each of which is coated with granular spinel particles which are in a state just like the state where the resulting spinel particles are in point-to-point contact as shown in FIG. 3. Thus, it is supposed that the size of the spinel particles may be eventually about 0.1 to 4 μm.

On the other hand, it is inferred that the firing which is carried out at an elevated temperature of 1,400° C. also allows proceeding of inter-particle fusion of and intra-particle crystallization of spinel particles, and thus may result in the formation of a spinel powder of particles, each of which is coated with granular spinel particles as shown in FIG. 4.

Figure 10:
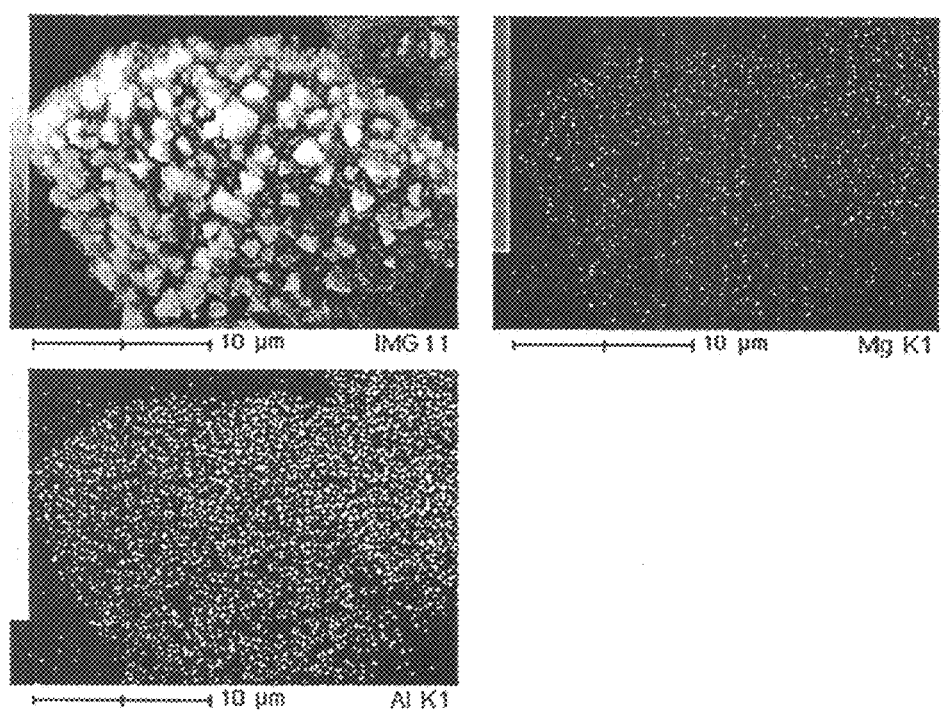
FIG. 10 is a micrograph (at a magnification of 3,000 times) of a particle of the spinel powder obtained in Example 1, and mappings showing the distribution of Mg and Al.

FIG. 10 shows a micrograph (at a magnification of 3,000 times) of a particle of the spinel powder obtained in Example 1 (left upper micrograph), along with views showing the distribution of Mg (right upper micrograph) and Al (left bottom micrograph). From these, it is found that the respective distributions of Mg and Al are almost uniform and each of the individual particles is a spinel.

A spinel powder of the present invention has a mean particle diameter D50 of about 10 to 70 μm, preferably about 15 to 60 μm, and particularly preferably about 20 to 50 μm, and a specific surface area of about 0.2 to 2 $m^2$/g, preferably about 0.3 to 1.5 $m^2$/g, and particularly preferably about 0.4 to 1 $m^2$/g.

A spinel powder having a mean particle diameter D50 of less than 10 μm is not preferable because flowability as a thermal spraying material cannot be ensured, while a spinel powder having a mean particle diameter D50 of more than 70 μm is not preferable because melting by plasma flame becomes unstable.

If the specific surface area is within the above-described range, then a spinel powder of the present invention can maintain characteristics of a thermal sprayed coating while improving its thermal spraying properties, as compared to fused spinels, and thus is suitable.

2. Method for Producing Spinel Powder

A method for producing a spinel powder of the present invention is characterized by mixing an electrically fused alumina with a magnesia raw-material, followed by firing of the mixture.

Preferably, the electrically fused alumina and the magnesia raw-material are mixed such that the content of alumina is 69 to 82% and the content of magnesia is 18 to 31% in the resulting spinel powder. If the respective contents of alumina and magnesia are within their ranges, then a spinel powder can be produced which is superior in thermal spraying property and can form a suitable sprayed coating.

As for the electrically fused alumina, there are not particular limitations, as long as it is an alumina which has been produced by electric melting. The electrically fused alumina preferably has a purity of about 99% or higher, particularly about 99.5% or higher. The electrically fused alumina has a mean particle diameter D50 of about 7 to 70 μm, preferably about 10 to 60 μm. If an electrically fused alumina has a mean particle diameter D50 within this range, then a spinel powder produced therefrom is capable of thermal spraying with ensuring its flowability as a thermal spraying material.

As for the magnesia raw-material, there are not particular limitations, as long as it is converted into magnesia by its firing. Examples include a magnesia, magnesium hydroxide, magnesium carbonate, and others. A magnesia is preferable because it is industrially mass-produced and is inexpensive. Particular preference is given to a light-burned magnesia with high reactivity which is produced by a seawater process. The purity of the magnesia raw-material is preferably about 97.5% or higher, except for water and ignition loss.

The mean particle diameter D50 of the magnesia raw-material is from about 1 to 10 μm, and preferably from about 2 to 8 μm. If a magnesia raw-material has a mean particle diameter D50 within this range, then the magnesia raw-material is capable of suitably reacting with an electrically fused alumina to form a spinel powder.

Methods for mixing an electrically fused alumina and a magnesia raw-material are not limited in particular. Any apparatus which allows their uniform mixing may be used, including a V-shaped mixer, a rocking mixer, a ribbon mixer, or the like, with a V-shaped mixers being particularly preferable because of its simple structure, small dead zone, and capability of uniform mixing.

In the present invention, coating aids, such as dispersants and binders, are not required for coating a magnesia raw-material onto an electrically fused alumina. However, such coating aids may be used as needed, within the purpose of the present invention.

Subsequently to mixing the electrically fused alumina and the magnesia raw-material, the mixture is fired to form a spinel powder.

The firing temperature is preferably from about 1,000 to 1,600° C., and particularly from about 1,200 to 1,400° C. Temperature of lower than 1,000° C. is not preferable because a necessary amount of the magnesia raw-material is not reacted completely. Temperature of higher than 1,600° C. is not preferable due to advancing of the sintering, making cracking of the resultant spinel powder difficult, and due to impairment of the flowability of the resultant spinel powder as a thermal spraying material.

The firing time is usually from about 1 to 6 hours, depending upon the firing temperature. For example, the firing time at 1,200° C. is preferably about 3 hours or more, and particularly about 3 to 6 hours. Firing time of less than 3 hours is not preferable because uneven firing is caused. In the present invention, it is preferable that the firing time is about 2 to 5 hours at 1,400° C. and about 1 to 3 hours at 1,600° C.

As for the atmosphere under which the firing is carried out, there are not particular limitations, and firing is usually performed under atmospheric pressure. After the firing is completed, the resulting spinel powder may not be subjected to any treatments; however, it is preferable that the resulting spinel powder is subjected to cracking using a small amount of a surface treatment agent such as alumina Aerosil, followed by classification.

Since an electrically fused alumina which is used as a raw material finds a very wide range of applications such as abrasives and refractories, particles of a powder of an electrically fused alumina which cannot be used in thermal spraying after the powder is subjected to classification for thermal spraying can be utilized in other applications, and thus the electrically fused alumina can be utilized very inexpensively. Therefore, the total cost can be significantly reduced and a thermal spraying powder can be produced at a reduced cost, even though the magnesia raw-material is mixed in a subsequent step, followed by allowing the reaction to achieve the spinelization. Furthermore, classification in advance into a particle size suitable for thermal spraying makes it possible for the particle size to be retained, even though a spinel is produced in a subsequent reaction. Therefore, there can be provided a spinel powder which is satisfied with its quality and cost.

3. Method for Producing Thermal Sprayed Film and Method for Producing Gas Sensor Element As mentioned above, a thermal sprayed film which is obtained by means of thermal spraying using a spinel powder which is produced by mixing a magnesia raw-material to an electrically fused alumina, followed by firing of the mixture, has an advantage that the film can be produced with much less variation in porosity and in a much more stable manner than for thermal sprayed films that are obtained using conventional, electrically fused powders. The reason therefor is that plasma spraying is process by which a film is formed on the surface of an element by introducing a spinel powder into a plasma flame having a temperature of higher than 5,000° C., and allowing the powder to be melted in a very short residence time, and the spinal particles produced by the present invention are characterized in that each of the particle is coated with granular spinel particles which are suitably dense inside, and by being capable of stably receiving the heat of the plasma flame. In consequence, the variation in characteristics of gas sensors can be reduced to a great extent.

Since an electrically fused alumina has a very wide range of applications such as abrasives and refractories, particles of a powder of an electrically fused alumina which cannot be used in thermal spraying after the powder is subjected to classification for thermal spraying can be utilized in other applications, and thus the electrically fused alumina can be utilized very inexpensively. Therefore, the total cost can be significantly reduced and a thermal spraying powder can be produced at a reduced cost, even though the magnesia raw-material is mixed in a subsequent step, followed by the reaction to achieve the spinelization. Furthermore, classification in advance into a particle size suitable for thermal spraying makes it possible for the particle size to be retained, even though a spinel is produced in a subsequent reaction. Therefore, there can be provided a spinel powder which is satisfied with its quality and cost.

EXAMPLES

Examples are given below and make the features of the present invention more clear. The present invention is not to be limited to the embodiments of the Examples.

[Measurement of Physical Properties]

In the Examples which follow, the physical properties described are measured by the methods described below.

(1) Mean Particle Diameter D50

Mean Particle Diameter D50 was measured using a laser diffraction/scattering instrument (LA-950, manufactured by HORIBA, Ltd.). In the present invention, a "mean particle diameter D50" refers to a particle diameter at which the accumulative percentage of the distribution of particle diameter measured is 50% by volume.

(2) Specific Surface Area

A specific surface area analyzer (Flowsorb II 2300, manufactured by SHIMADZU CORPORATION) was used to measure the specific surface area by the BET method.

Example 1

Into a 10-L V-shaped mixer were charged 3.67 kg of an electrically fused alumina having a purity of 99.5% or higher and a particle diameter of 20.6 µm (WA#800, manufactured by Ujiden Kagaku Kogyo) and 1.38 kg of a magnesium oxide having a purity of 97.5% or higher (excepting water and ignition loss) and a particle diameter of 7.0 µm (STARMAG U, manufactured by Konoshima Chemical Co., Ltd.). The mixture was mixed for 30 minutes, and then subjected to firing under atmospheric pressure at 1,250° C. for 4 hours to produce a spinel powder.

The spinel powder thus produced and 20 g of alumina Aerosil were placed into a V-shaped mixer. The mixture was subjected to mixing and cracking for 30 minutes, followed by sieving through a 90-µm screen to give a spinel powder as the final product. The spinel powder finally obtained had a bulk specific gravity of 1.27 g/cm$^3$, and specific surface areas D50, D90, and D10 of 26.8 µm, 39.8 µm, and 18.4 µm, respectively.

This spinel powder had a specific surface area of 0.7 m$^2$/g. For comparison, a spinel powder by electric melting had a specific surface area of approximately 0.1 m$^2$/g. It turns out that the present invention provided a spinel powder with an about 7-fold higher specific surface area.

Figure 11:
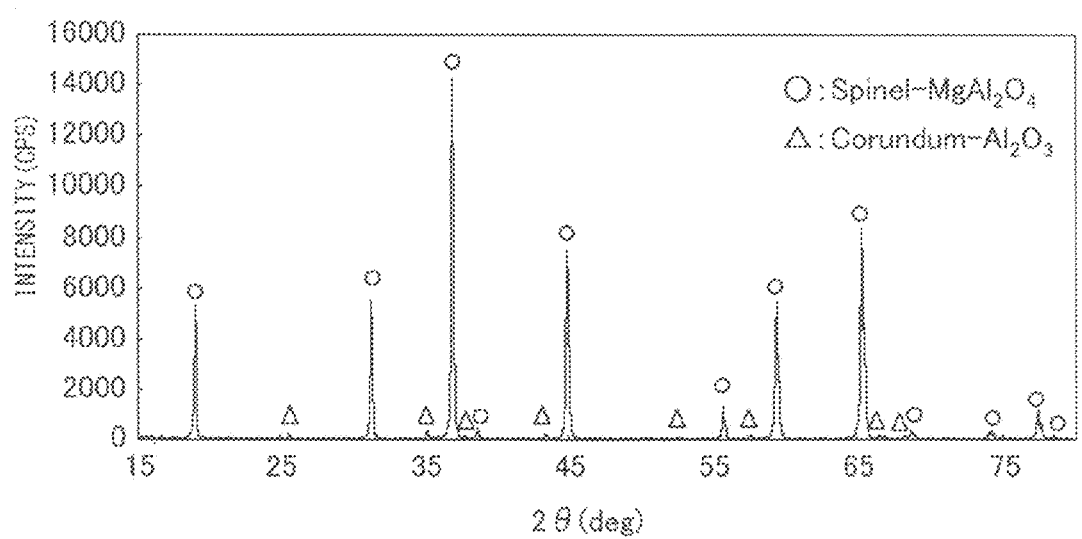
FIG. 11 is an XRD pattern of the spinel powder obtained in Example 1.

FIG. 11 represents an XRD pattern of the spinel powder obtained by the present invention, showing that although the presence of some amounts of corundum is identified, the absence of periclase is identified, and thus an almost perfect spinel has been formed. The spinel powder had an X-ray diffraction intensity ratio: a ratio $I[\alpha Al_2O_3(113)]/\{I[\alpha Al_2O_3(113)]+I[MgAl_2O_4(311)]\}$ of 0.013.

Example 2

A spinel powder was obtained in a similar way as in Example 1, except that the firing was performed at 1,400° C. The spinel powder obtained had a bulk specific gravity of 1.30 g/cm$^3$, and specific surface areas D50, D90, and D10 of 26.5 µm, 37.8 µm, and 18.1 µm, respectively. This spinel powder had a specific surface area of 0.3 m$^2$/g.

Example 3

In the present example, description will be made with respect to an example in which the spinel powder prepared in Example 1 is thermally sprayed onto a gas sensor element. Description will be made with respect to Example relating to a gas sensor element of the present invention and a gas sensor including the same built therein, with reference to FIG. 12 and FIG. 13.

Figure 12:
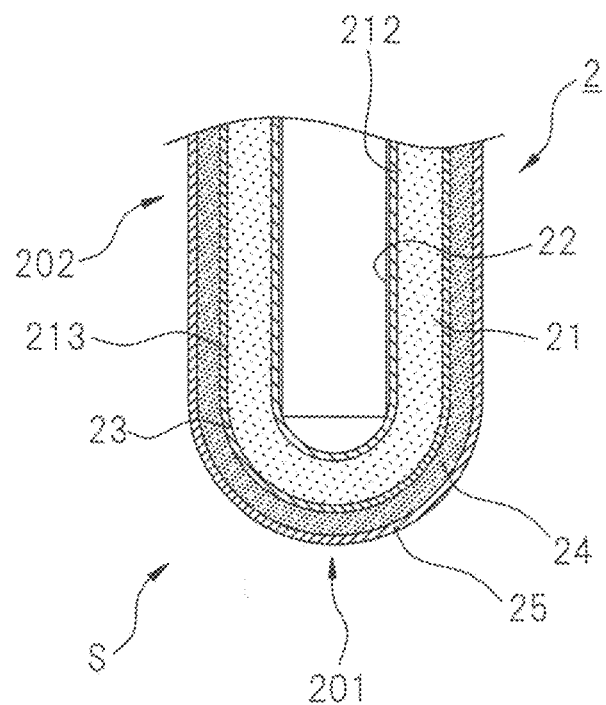
FIG. 12 is a cross-sectional view of a gas sensor element used in Examples 3, 4, and 5.
Figure 13:
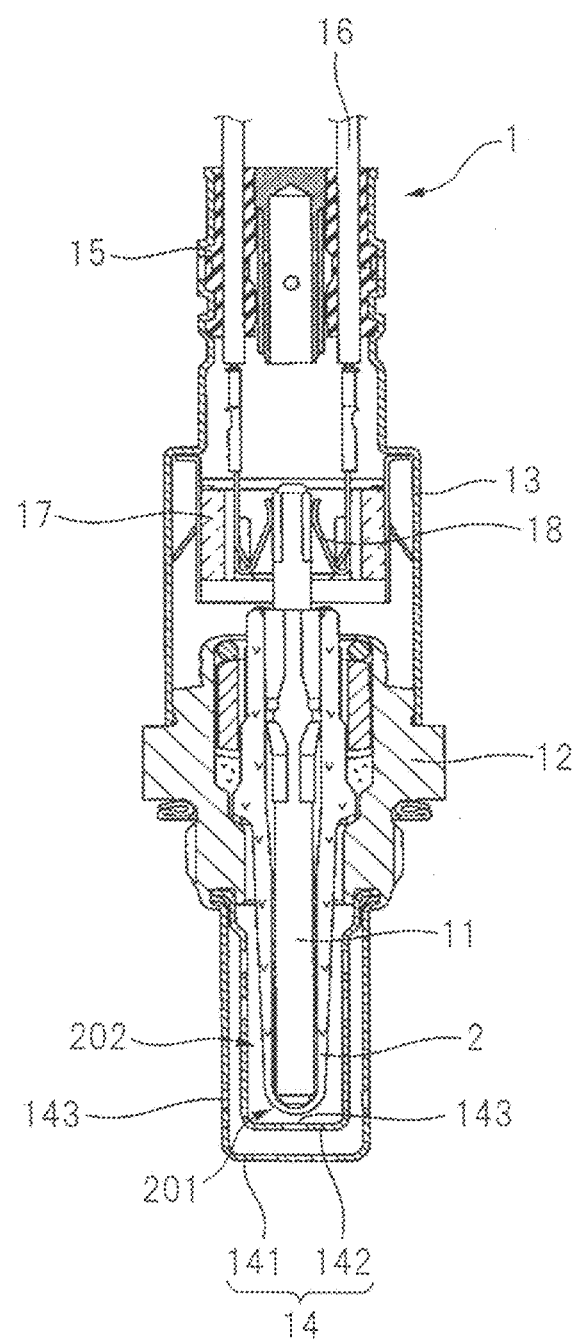
FIG. 13 is a cross-sectional view of a gas sensor used in Examples 3, 4, and 5.

As shown in FIG. 12, a gas sensor element 2 of the present example includes a bottomed cylindrical oxygen ion conductive solid electrolyte 21; a reference electrode 22 provided on an inner surface 212 of the solid electrolyte 21; a measurement electrode 23 provided on an outer surface 213 of the solid electrolyte 21; and a protective layer 24, which covers the outer surface 213 of the solid electrolyte 21, including a measurement electrode 23, and allows penetration of a gas to be measured; and is built in a gas sensor 1 (FIG. 13).

On a tip side of the gas sensor element 2, as shown in FIG. 12, a leg 202 in which a contour line in an axial section S parallel to an axial direction of this gas sensor element is a straight line, and a bottom 201 in which the contour line is a curved line are formed.

In more detail, as shown in FIG. 13, the gas sensor 1 of the present example includes, in addition to the gas sensor element 2; a heater 11 which is inserted into a solid electrolyte 21 and is heating by energization; a housing 12 which supports the gas sensor element 2 inserted thereinto; an atmosphere side cover 13 which is provided on the base end side of the housing 12 and covers the base end side of the gas sensor element 2; and an element cover 14 which is provided on the tip side and covers the tip side of the gas sensor element 2.

Furthermore, the gas sensor 1 includes an atmosphere side insulator 17 which is provided so as to cover the base end side of the gas sensor element 2; a bush 15 which is provided on the base end side of the atmosphere side cover 13, a lead 16 which is inserted into the bush 15; and a metal fitting 18 which is connected with the lead 16 and is electrically connected with a heater 11 and a gas sensor element 2.

The element cover 14 includes a gas introducing hole 143 on the bottom and side portions, as shown in FIG. 13. Specifically, the element cover 14 serves as a double cover, and an outer cover 141 and an inner cover 142 are staked to each other on the tip portion of the housing 12. Then, a gas to be measured introduced into the space between the outer cover 141 and the inner cover 142 through gas introducing hole 143 provided in the outer cover 141 is further introduced into the element cover 14 through the gas introducing hole 143 provided in the inner cover 142. In the inner cover 142, the gas introducing hole 143 is formed on the further tip side of the bottom 201 of the protective layer 24.

The gas sensor element 2 to be built in the gas sensor 1 will be described in detail below.

The gas sensor element 2 used in the present example includes a wide-range air-fuel ratio sensor element built in an air-fuel ratio sensor to be used in an exhaust gas feedback system, and an oxygen concentration sensor element configured to measure the concentration of oxygen in an exhaust gas, after providing in an exhaust pipe of an internal combustion engine for various vehicles such as an automotive engine. As mentioned above, the gas sensor element 2 includes, in addition to the solid electrolyte 21, the reference electrode 22, the measurement electrode 23 and the protective layer 24, a trap layer 25 which covers an outer surface of the protective layer 24. The trap layer 25 can be formed by using metal oxides which contains, in addition to γ alumina, θ alumina or the like, containing zirconia or titania as a main component. The trap layer 25 can be formed by dipping the gas sensor element 2.

In the present example, as shown in Table 1, samples 1 to 10, which are gas sensor elements including a protective film formed by using a thermal spraying powder (electrically fused product) of the prior art and a thermal spraying powder (developed product) according to the present invention, were evaluated.

A spinel powder in the present example will be described. In order to adjust the porosity to a desired value, a thermal spraying powder aiming at various mean particle diameters was prepared. Since a variation in particle diameter is also important, a thermal spraying powder was prepared in which particles having a particle diameter within ±50% of each median particle diameter accounts for 80% or more.

Conditions of a test of forming a protective film by plasma thermal spraying in the present example will be described. Using a plasma thermal spraying gun (F4MB: manufactured by Sulzer Metco Inc.), an electric current of 425 A and a voltage of 60 V are applied to the place where a primary working gas (Ar) flows at a flow rate of 16SLM and a secondary working gas ($N_2$) flows at a flow rate of 12SLM to generate plasma jet. A thermal spraying powder is fused by supplying to the plasma jet at 20 g/min, and then sprayed over a gas sensor element rotating around an axis in a longitudinal direction at 500 rpm. At this time, a protective film was formed on the gas sensor element (30 samples per each level) at a distance between a spout port of the thermal spraying gun and the gas sensor element of 110 mm in a target film thickness of 300 μm.

Evaluation items, methods, and evaluation criteria of the present example will be described below. The film thickness was measured at the position, which is 5 mm away from a tip of the gas sensor element, by a laser displacement sensor (manufactured by KEYENCE CORPORATION). A result in which variation in film thickness is within 300±30 μm was expressed with "good". Using a mercury press-in method (AUTOPORE: manufactured by Shimadzu Corporation), porosity was evaluated. A result in which the mean value is within ±10% based on a target value was expressed with "good". Yield was calculated by the formula: 100×(weight of protective film)/(supply amount of thermal spraying powder). A result in which the yield is 5% or more was expressed with "good".

TABLE 1

| | Thermal spraying powder | | | Protective film | | | |
| --- | --- | --- | --- | --- | --- | --- | --- |
| | | | | Target | | Variation | |
| No. | Thermal spraying powder | Particle size (D50) | Specific surface area | porosity value | Porosity | in film thickness | Yield |
| 1 | Developed powder | 5.3 μm | 1.65 m²/g | 4% | Good | Bad | Bad |
| 2 | Developed powder | 10.2 μm | 1.35 m²/g | 4% | Good | Good | Good |
| 3 | Developed powder | 20.6 μm | 0.96 m²/g | 5% | Good | Good | Good |
| 4 | Developed powder | 40.1 μm | 0.45 m²/g | 7% | Good | Good | Good |
| 5 | Developed powder | 50.5 μm | 0.35 m²/g | 8% | Good | Good | Good |
| 6 | Developed powder | 60.7 μm | 0.31 m²/g | 10% | Good | Good | Good |
| 7 | Developed powder | 59.3 μm | 0.31 m²/g | 15% | Good | Good | Good |
| 8 | Developed powder | 80.6 μm | 0.29 m²/g | 15% | Bad | Bad | Bad |
| 9 | Electrically fused powder | 21 μm | 0.10 m²/g | 5% | Bad | Bad | Bad |
| 10 | Electrically fused powder | 40.5 μm | 0.08 m²/g | 7% | Bad | Bad | Bad |

As is apparent from the results shown in Table 1, in the formation of an electrode protecting film of a gas sensor element using a spinel powder obtained by mixing an electrically fused alumina with a magnesia raw-material, followed by firing of the mixture, if a particle diameter is within a range from 10 μm to 70 μm, it is possible to obtain satisfactory results in important characteristics for a gas sensor, such as porosity, variation in film thickness, and material yield, as compared to a protective film using a conventional electrically fused powder.

Examples 4 and 5

In the following Examples 4 and 5, effect as a gas sensor was verified. A gas sensor to be mounted on an automobile is used as a part of an exhaust gas purification system in which the concentration of oxygen in an exhaust gas is detected, followed by giving of feedback and further controlling of a mixing ratio of a fuel to air. In order to cope with the exhaust gas purification system which varies depending on an automobile manufacturer, a gas sensor capable of coping with the system is needed. Therefore, variation in characteristics of a gas sensor (Example 4) with comparatively low responsiveness and a gas sensor (Example 5) with comparatively high responsiveness was evaluated.

Example 4

Under thermal spray conditions similar to those in Example 3, 300 μm protective films were formed using a conventional, electrically fused powder having a D50 of 26.5 μm and the powder developed in Example 1 having a D50 of 26.8 μm, and then characteristics and variation ratio of the sensor were compared. For sensor characteristics, measured as a response time was the cycle when the sensor output was examined by supplying alternatively each of gases simulating an actual automobile gas of a rich atmosphere and of a lean atmosphere under conditions where the detection portion of the sensor element was heated to 400° C. A result in which the response time was 2.0 seconds or less and 30 sensors gave values with a variation of 5% or less for each of the gases was expressed with "good". The gas simulating an actual automobile gas was supplied such that for the rich gas, CO, $CH_4$, and $C_3H_8$ were set to be at $\lambda=0.99$, and for lean gas, $O_2$ and NO at $\lambda=1.01$. For variation in characteristics, a duration test was carried out under duration conditions of 950° C. for 1,500 hours. A result in which sensors gave values with a variation of 5% or less between before and after duration was expressed with "good". The porosity, variation in film thickness, and material yield were evaluated in a similar way as in Example 3.

the sensor responsiveness, and gas sensor elements can be produced at a reduced cost, when a spinel powder is used which is formed by mixing the magnesia raw-material to the electrically fused alumina, followed by firing of the mixture, as compared to a protective film which is formed using conventional powders produced by electric melting.

Example 5

Under thermal spray conditions similar to those in Example 4, 100 μm protective films were formed using a conventional, electrically fused powder having a D50 of 40.5 μm and the powder developed in Example 1 having a D50 of 40.1 μm, and compared as in Example 5.

For sensor characteristics, measured as a response time was the cycle when the sensor output was examined by supplying alternatively each of gases simulating an actual automobile gas of a rich atmosphere and of a lean atmosphere under conditions where the detection portion of the sensor element was heated to 400° C. A result in which the response time was 1.2 seconds or less and 30 sensors gave values with a variation of 5% or less for each of the gases was expressed with "good". The gas simulating an actual automobile gas

TABLE 2

| | Thermal spraying powder | | | Protective film | | | | Sensor |
|---|---|---|---|---|---|---|---|---|
| | | | | Target | | Variation | | |
| No. | Thermal spraying powder | Particle size (D50) | Specific surface area | porosity value | Porosity | in film thickness | Yield | characteristics Response time |
| 11 | Developed powder | 26.8 μm | 0.70 m²/g | 6% | Good | Good | Good | Good |
| 12 | Electrically fused powder | 26.5 μm | 0.10 m²/g | 6% | Bad | Bad | Bad | Bad |

As is apparent from the results shown in Table 2, gas sensors in which a 300 μm protective film is formed using a thermal spraying raw-material which has a particle size range of about 26 μm result in a great reduction in the variation of was supplied such that for the rich gas, CO, $CH_4$, and $C_3H_8$ were set to be at $\lambda=0.99$, and for lean gas, $O_2$ and NO at $\lambda=1.01$. The porosity, variation in film thickness, and material yield were evaluated in a similar way as in Example 3.

TABLE 3

| | Thermal spraying powder | | | Protective film | | | | Sensor |
|---|---|---|---|---|---|---|---|---|
| | | | | Target | | Variation | | |
| No. | Thermal spraying powder | Particle size (D50) | Specific surface area | porosity value | Porosity | in film thickness | Yield | characteristics Response time |
| 13 | Developed powder | 40.1 μm | 0.45 m²/g | 7% | Good | Good | Good | Good |
| 14 | Electrically fused powder | 40.5 μm | 0.08 m²/g | 7% | Bad | Bad | Bad | Bad |

As is apparent from the results shown in Table 3, gas sensors in which a 100 μm protective film is formed using a thermal spraying raw-material which has a particle size range of about 40 μm result in a great reduction in the variation of the sensor responsiveness, and gas sensor elements can be produced at a reduced cost, when a spinel powder is used which is formed by mixing the magnesia raw-material to the electrically fused alumina, followed by firing of the mixture, as compared to a protective film which is formed using conventional powders produced by electric melting.

INDUSTRIAL APPLICABILITY

According to the present invention, a spinel powder and a simple method for producing the same can be provided, which is superior in thermal spraying property and has a unique particle shape, and particularly a method for producing a spinel powder which contributes to a reduction in the variation of characteristics of sensors, for example, as a thermal spraying powder for forming a protective coating of a gas sensor element.

DESCRIPTION OF REFERENCE NUMERALS

1: Gas sensor
2: Gas sensor element
11: Heater
12: Housing
13: Atmosphere side cover
14: Element cover
15: Bush
16: Lead
17: Atmosphere side insulator
18: Metal fitting
21: Solid electrolyte
22: Reference electrode
23: Measurement electrode
24: Protective layer
25: Trap layer

The invention claimed is:

1. A spinel powder coated with granular spinel particles, wherein the granular spinel particles are from 0.1 to 4 μm, and the spinel powder has a mean particle diameter D50 of 10 to 70 μm and a specific surface area of 0.2 to 2 m$^2$/g.

2. The spinel powder according to claim 1, wherein the spinel powder has an alumina content of 69 to 82% and a magnesia content of 18 to 31%.

3. The spinel powder according to claim 1, wherein the spinel powder has X-ray diffraction intensity ratios:
   a ratio I[αAl$_2$O$_3$(113)]/{I[αAl$_2$O$_3$(113)]+I[MgAl$_2$O$_4$(311)]} of 0.03 or less, and
   a ratio I[MgO(200)]/{I[MgO(200)]+I[MgAl$_2$O$_4$(311)]} of 0.03 or less.

4. A method for producing a spinel powder according to claim 1, which comprises mixing a magnesia raw-material with an electrically fused alumina, followed by firing of the mixture.

5. The method for producing a spinel powder according to claim 4, wherein the spinel powder has an alumina content of 69 to 82% and a magnesia content of 18 to 31%.

6. The method for producing a spinel powder according to claim 4, wherein the electrically fused alumina has a mean particle diameter D50 of 7 to 70 μm and the magnesia raw-material has a mean particle diameter D50 of 1 to 10 μm.

7. A method for producing a thermal sprayed film, which comprises performing thermal spraying using a spinel powder described in claim 1, the spinel powder being produced by mixing a magnesia raw-material with an electrically fused alumina, followed by firing of the mixture.

8. A method for producing a gas sensor element, which comprises forming an electrode-protecting film of the gas sensor element using a spinel powder described in claim 1, the spinel powder being produced by mixing a magnesia raw-material with an electrically fused alumina, followed by firing of the mixture.

9. The spinel powder according to claim 2, wherein the spinel powder has X-ray diffraction intensity ratios:
   a ratio I[αAl$_2$O$_3$(113)]/{I[αAl$_2$O$_3$(113)]+I[MgAl$_2$O$_4$(311)]} of 0.03 or less, and
   a ratio I[MgO(200)]/{I[MgO(200)]+I[MgAl$_2$O$_4$(311)]} of 0.03 or less.

10. The method for producing a spinel powder according to claim 2, which comprises mixing a magnesia raw-material with an electrically fused alumina, followed by firing of the mixture.

11. The method for producing a spinel powder according to claim 3, which comprises mixing a magnesia raw-material with an electrically fused alumina, followed by firing of the mixture.

12. The method for producing a spinel powder according to claim 5, wherein the electrically fused alumina has a mean particle diameter D50 of 7 to 70 μm and the magnesia raw-material has a mean particle diameter D50 of 1 to 10 μm.

13. A method for producing a thermal sprayed film, which comprises performing thermal spraying using a spinel powder described in claim 2, the spinel powder being produced by mixing a magnesia raw-material with an electrically fused alumina, followed by firing of the mixture.

14. A method for producing a thermal sprayed film, which comprises performing thermal spraying using a spinel powder described in claim 3, the spinel powder being produced by mixing a magnesia raw-material with an electrically fused alumina, followed by firing of the mixture.

15. A method for producing a gas sensor element, which comprises forming an electrode-protecting film of the gas sensor element using a spinel powder described claim 2, the spinel powder being produced by mixing a magnesia raw-material with an electrically fused alumina, followed by firing of the mixture.

16. A method for producing a gas sensor element, which comprises forming an electrode-protecting film of the gas sensor element using a spinel powder described claim 3, the spinel powder being produced by mixing a magnesia raw-material with an electrically fused alumina, followed by firing of the mixture.

* * * * *